United States Patent [19]

Berg et al.

[11] Patent Number: 4,520,218
[45] Date of Patent: May 28, 1985

[54] PRODUCTION OF DIALKYLATED AROMATICS

[75] Inventors: Roy C. Berg, Park Ridge; Thomas P. Malloy, Lake Zurich; Bipin V. Vora, Elk Grove Village, all of Ill.

[73] Assignee: UOP Inc., Des Plaines, Ill.

[21] Appl. No.: 582,657

[22] Filed: Feb. 23, 1984

[51] Int. Cl.³ .............................................. C07C 2/64
[52] U.S. Cl. .................................... 585/449; 585/464
[58] Field of Search ................................ 585/449, 464

[56] References Cited

U.S. PATENT DOCUMENTS

| 2,477,382 | 7/1949 | Lewis | 585/464 |
| 3,349,144 | 10/1967 | Alul et al. | 585/464 |
| 3,494,971 | 2/1970 | Fenske | 585/449 |
| 3,830,865 | 8/1974 | Anderson | 585/464 |
| 3,927,134 | 12/1975 | Yanaqihara et al. | 585/464 |
| 3,950,448 | 4/1976 | Witt | 585/449 |
| 4,046,516 | 9/1977 | Burton et al. | 585/449 |
| 4,225,737 | 9/1980 | Mikulicz et al. | 585/449 |

Primary Examiner—Curtis R. Davis
Attorney, Agent, or Firm—William H. Page, II; John F. Spears, Jr.

[57] ABSTRACT

A process is disclosed for producing a mixture of mono- and diallkylated aromatic hydrocarbons suitable for use as a detergent or as a surfactant in enhanced oil recovery processes. Two alkylation reaction stages are used in series, with a separate amount of an acyclic olefin being charged to each reaction stage. The effluent of the second alkylation reaction stage is separated by fractionation to form a mixture of mono- and dialkylated hydrocarbons. A portion of this mixture is recycled to the second alkylation reaction stage, with remainder being withdrawn as the product stream.

16 Claims, 1 Drawing Figure

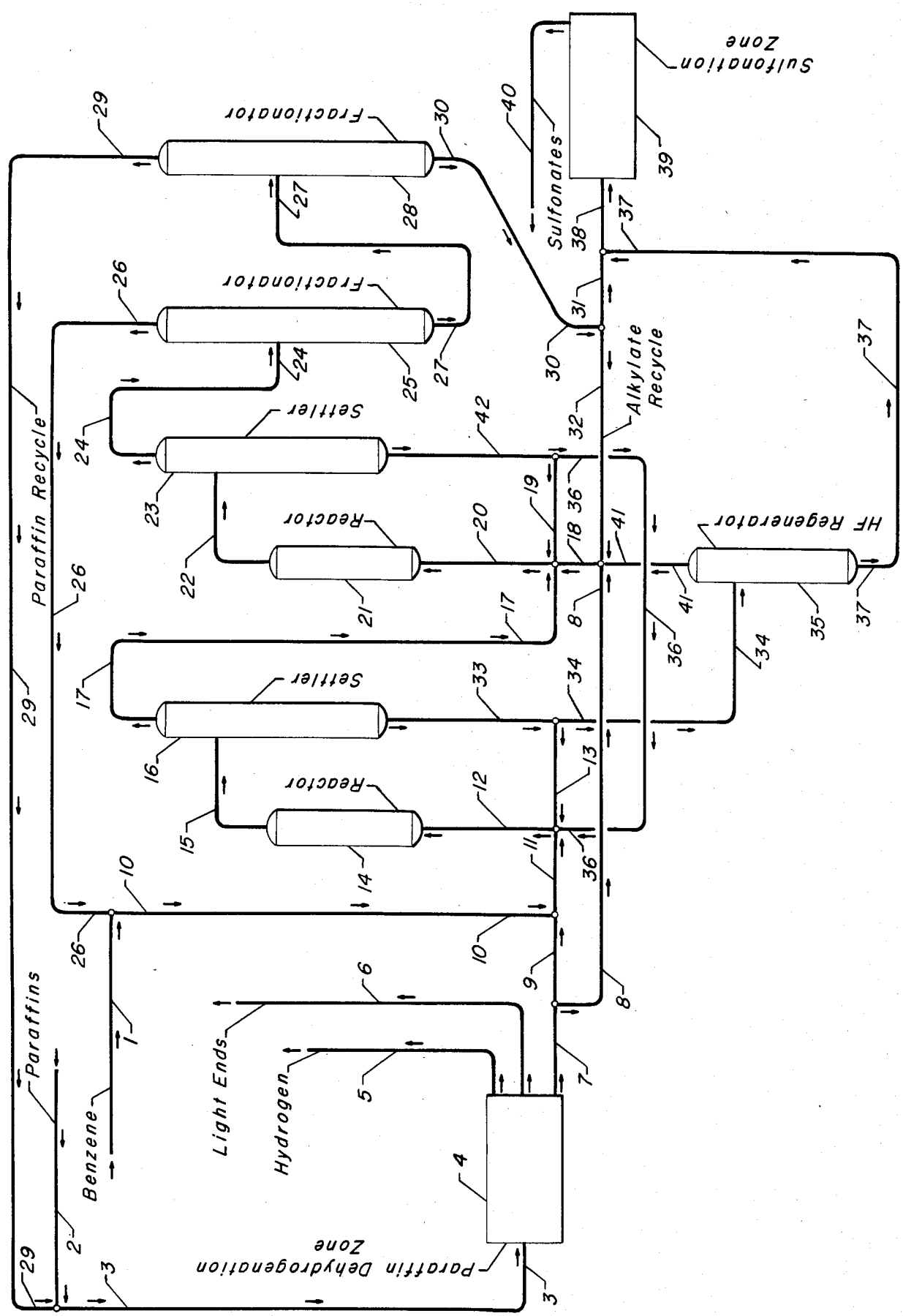

PRODUCTION OF DIALKYLATED AROMATICS

FIELD OF THE INVENTION

The invention relates to a hydrocarbon conversion process. More specifically, the invention relates to a process for producing a blend of mono- and dialkylated aromatic hydrocarbons by the reaction of an aromatic hydrocarbon with an acyclic olefinic hydrocarbon. An example of this is the reaction of benzene with a $C_8$ to $C_{22}$ normal olefin. The subject invention is directed to the use of an acid catalyst and preferably employs liquid phase HF as the catalyst. The invention also relates to such a process which includes the production of the acyclic olefin by the catalytic dehydrogenation of a corresponding normal paraffin.

INFORMATION DISCLOSURE

The alkylation of benzene with acyclic olefins is a widely practiced commercial process. This process may be performed to produce a large variety of chemical compounds which may be end products or intermediates. One of the most significant aromatic alkylation processes uses HF as the catalyst and is performed to produce linear alkylbenzenes which are then converted into detergents as by sulfonation. This process is described in some detail in U.S. Pat. No. 2,477,382 issued to A. H. Lewis. Another early reference in this area is U.S. Pat. No. 3,349,144 issued to H. R. Alul et al. This latter reference provides improved operating conditions for the alkylation reaction of benzene with linear $C_6$ to $C_{20}$ olefins and describes the production of these olefins by the catalytic dehydrogenation of paraffins. The reference also indicates that the mixture of parafins and olefins produced in the dehydrogenation zone may be passed directly into the alkylation zone and that the unreactive paraffins can then be separated from the alkylation zone effluent and recycled.

U.S. Pat. No. 3,494,971 issued to E. R. Fenske illustrates a process for the production of monoalkylated aromatic hydrocarbons using two alkylation stages in series. U.S. Pat. Nos. 3,830,865 issued to R. F. Anderson and 4,225,737 issued to M. Z. Mikulicz also show two alkylation stages in a series flow arrangement. These latter two references are also pertinent for showing the addition of feed olefin to each alkylation stage. The feed aromatic hydrocarbon may be chosen from a variety of compounds including benzene, toluene, xylene and ethylbenzene. It is pertinent to note that it is indicated in these references that the addition of the feed olefin to each alkylation stage is advantageous to reduce the fractionation costs inherent in employing a high aromatic hydrocarbon to olefinic hydrocarbon mole ratio. This high ratio is stated to be desirable to increase the quality of the product alkylate.

U.S. Pat. No. 3,950,448 issued to P. A. Witt is pertinent for its showing of a representative arrangement of commercial fractionation systems used to recover noalkylated aromatic hydrocarbons in alkylation processes similar to those described above. This reference also illustrates the use of a stripping column to regenerate HF used as the alkylation catalyst.

BRIEF SUMMARY OF THE INVENTION

The subject process provides a process for the production of a mixture of mono- and dialkylated aromatic compounds which also provides for accurate and convenient control of the ratio of di- to monoalkylated compounds. A broad embodiment of the process comprises the steps of reacting a feed aromatic hydrocarbon and a first portion of a feed acyclic olefinic hydrocarbon in the first alkylation stage of a multi-stage alkylation zone maintained at alkylation-promoting conditions and thereby producing a first alkylation stage effluent stream which comprises the feed aromatic hydrocarbon and a monoalkylated aromatic hydrocarbon; passing the first alkylation stage effluent stream, a hereinafter characterized recycle stream and a second portion of the feed acyclic olefinic hydrocarbon into a subsequent second alkylation stage of the alkylation zone maintained at alkylation-promoting conditions and thereby effecting the further alkylation of monoalkylated aromatic hydrocarbons and the production of a second alkylation stage effluent stream which comprises the feed aromatic hydrocarbon, the monoalkylated hydrocarbon and a dialkylated hydrocarbon; fractionating an alkylation zone effluent stream which comprises the feed aromatic hydrocarbon, the monoalkylated hydrocarbon and the dialkylated aromatic hydrocarbon in a fractionation zone and thereby producing a first process stream which comprises the monoalkylated aromatic hydrocarbon and the aromatic dialkylated hydrocarbon; and withdrawing a first portion of the first process stream as a product stream and passing a second portion of the first process stream into the second alkylation stage as the previously referred to recycle stream.

BRIEF DESCRIPTION OF THE DRAWING

The drawing is a simplified process flow diagram of the preferred embodiment of the invention. A feed stream comprising a high purity limited carbon number range mixture of normal paraffins enters the process through line 2. This feed stream is admixed with the recycle paraffin stream carried by line 29 and passed into the paraffin dehydrogenation zone 4 through line 3. In this zone the entering paraffins are contacted with a dehydrogenation catalyst to effect the conversion of the feed paraffins to the corresponding normal olefins having the same number of carbon atoms per molecule. There is thereby produced a net hydrogen stream removed from the dehydrogenation zone through line 5, a light ends stream removed from a stripping column within the dehydrogenation zone through line 6 and a net paraffin dehydrogenation zone effluent stream comprising a mixture of normal paraffins and normal olefins and removed through line 7.

A first portion of the dehydrogenation zone effluent stream is passed through line 9 and combined with a benzene-containing liquid stream carried by line 10. This admixture of normal paraffins, normal olefins and benzene flows through line 11 before it is admixed with the streams of HF flowing through lines 13 and 36 and then passed into a first reaction vessel 14 through line 12. The HF acts as a catalyst which promotes the alkylation of the benzene with the normal olefinic hydrocarbons. This reaction is performed at turbulent conditions which produce an admixture of HF and hydrocarbons which is removed from the reaction vessel 14 through line 15 and passed into a first settling zone 16. The quiescent conditions maintained within the settler 16 result in the separation of the denser liquid phase HF from the hydrocarbons, with the HF being withdrawn from the bottom of the settler through line 33. This HF stream is divided into a first portion passed into the first reaction vessel via line 13 and a smaller second portion which is passed into the HF regenerator 35 through line 34. The HF entering the HF regenerator, which is basically a stripping column, is separated into an overhead stream comprising high purity HF carried by line 41 and a net bottoms stream comprising an admixture of high boiling hydrocarbons. Light hydrocarbons which enter the HF regenerator are removed overhead and separated via a line not shown.

The hydrocarbons which enter the settler 16 are removed as a hydrocarbon stream carried by line 17 which comprises an admixture of benzene, normal paraffinic hydrocarbons and monoalkylated benzene. This stream is essentially devoid of the feed olefinic hydrocarbons. This admixture is admixed with the contents of line 18 which comprise a second portion of the paraffin dehydrogenation zone effluent stream from line 8, high purity HF from line 41 and an alkylate recycle stream carried by line 32 and which comprises a mixture of mono- and dialkylated benzene. Liquid phase HF carried by line 19 is also admixed into these hydrocarbons and these materials are then passed upward into a second reaction vessel 21 through line 20.

The reaction conditions maintained in the second reaction vessel result in the alkylation of an additional amount of the entering benzene but also result in the alkylation of a significant portion of the monoalkylated benzene which enters this reaction zone. A mixture comprising liquid phase HF, the normal paraffins, benzene and mono- and dialkylated aromatics is removed from the second reaction vessel and passed through line 22 into the second settler 23. As in the first alkylation stage, the denser liquid phase HF accumulates as a lower liquid phase which is withdrawn through line 42. A first portion of this HF is returned to the second reaction vessel through line 19 and a second portion is passed into the first reaction vessel 14 through line 36.

Liquid phase hydrocarbons are withdrawn from the second alkylation stage in line 24 as the effluent of the alkylation zone and are passed into a first fractionation column 25. This first fractionation column, which is also referred to as a benzene stripping column, concentrates essentially all of the benzene and the dissolved HF which enters the column into a net overhead stream carried by line 26. This net overhead stream of recycle benzene is combined with the feed benzene stream entering the process through line 1 to form the benzene stream passed into the first alkylation stage. Those hydrocarbons which are less volatile than benzene are separated into a net bottoms stream which is removed from the first fractionation column in line 27 and passed into an intermediate point of a second fractionation column 28, which is referred to as the paraffin column. The paraffinic hydrocarbons which enter the fractionator 28 are therein separated into a net overhead stream transported through line 29 for recycling to the paraffin dehydrogenation zone 4. The remaining hydrocarbons essentially comprise a mixture of monoa- and dialkylated benzene which is withdrawn from the fractionation column 28 through line 30. A first major portion of this mixture is recycled through line 32 to the second alkylation stage to effect the conversion of monoalkylated benzenes to dialkylated benzenes. A remaining major portion of the bottoms of the fractionator 28 is withdrawn through line 31 and admixed with neutralized heavy hydrocarbons from line 37 to form a net product stream which is passed into a sulfonation zone 39 through line 38. The sulfonation zone is operated at conditions effective to convert entering compounds into a sulfonate product removed through line 40 which can be used directly or can be converted to a water-soluble salt.

DETAILED DESCRIPTION OF THE INVENTION

As already described, the alkylation of aromatic hydrocarbons through the use of a mineral acid is a well developed process for the production of surfactant precursors. The alkylation of benzene with a straight chain normal olefin is the favored form of this process since the alkylate will yield a biodegradable or "soft" detergent. A slightly different form of the process utilizes as the olefinic hydrocarbon a dimer or trimer of propylene or butylene. This dimer or trimer is normally a branched olefin and the detergent manufactured from an alkylation process consuming this olefin is normally not biodegradable. The biodegradability of the resultant detergent becomes a very important factor in choosing the composition and process for the production of a detergent alkylate.

The present high cost of crude oil combined with advances in techniques for enhanced oil recovery have led to either proposals for or the actual initiation of rather large scale enhanced oil recovery projects. In many of these projects, a surfactant is employed to promote the release of the crude oil from the oil-bearing geologic structure in which it is located. Since a significant amount of the surfactant would not be recovered but will remain in this geologic structure and the remainder of the surfactant will become part of the recovered crude oil, the biodegradability of the surfactant becomes much less important. The primary characteristics used in evaluating a surfactant for use in enhanced oil recovery are basically the cost of the surfactant and the effectiveness of the surfactant. A description of the use of surfactants in enhanced oil recovery and some criteria for evaluating the surfactants are contained in U.S. Pat. Nos. 4,245,700 and 4,330,418. As pointed out in these references, in some instances it may be desirable to utilize a high molecular weight dialkylated aromatic compound as the surfactant precursor. It is therefore an objective of the subject invention to provide a commercially practical process for the production of dialkylated benzene suitable for use as enhanced oil recovery detergent precursors. A further objective of the subject invention is to provide a process for the production of detergent precursors comprising an admixture of mono- and dialkylated aromatic hydrocarbons.

The subject process utilizes a multi-stage alkylation zone. The alkylation zone may contain three or more separate alkylation stages, but preferably contains two alkylation stages arranged in series flow in the manner illustrated in the drawing. As used herein, the term "alkylation stage" is intended to refer to an assemblage of process equipment which provides an initial contacting area or zone wherein the reactants are brought into contact with liquid phase mineral acids at alkylation-promoting conditions which include a significant amount of turbulence followed by a separation zone or area in which liquid phase HF is separated from liquid phase hydrocarbons by decantation. An alkylation stage therefore is in many aspects similar to the mixer-settler stages which may be employed in a liquid-liquid extraction process. Each alkylation stage may be further characterized by the fact that a stream of the olefinic hydrocarbon consumed within the alkylation reaction is passed into the reaction zone or compartment of the alkylation stage. This olefinic stream may enter the alkylation stage at a single point as by admixture into the hydrocarbon stream entering into the alkylation stage, or the olefin feed material may be charged to the alkylation stage at a number of points along the flow path of the hydrocarbon stream through the reaction area of the alkylation stage.

The reaction zone of each alkylation stage is maintained at alkylation-promoting conditions. As used herein, the term "alkylation-promoting conditions" is intended to include a pressure sufficient to maintain the hydrocarbon reactants and HF in a liquid phase. A general range operating pressure is from about 2 to about 41 atmospheres absolute. A pressure below about 30 atmospheres absolute is preferred. Alkylation-promoting conditions also include a temperature within the broad range of from about $-20°$ to about 95° C., but the reaction is preferably conducted at a temperature of from about 10° to about 60° C. A temperature of about 40° C. is especially preferred. These operating temperatures and pressures are preferred for all alkylation stages employed within the process. The volumetric ratio of liquid phase HF to the total amount of hydrocarbon entering the reaction zone of each alkylation zone should be maintained within the broad range of from about 0.1:1 to about 4:1. A preferred range for this ratio is from about 0.25:1 to 2:1. These ratios may be employed in each alkylation stage of the alkylation zone.

It is often taught in references dealing with the HF-promoted alkylation of benzene that it is desirable to maintain a molar excess of benzene over the straight chain olefinic hydrocarbon consumed in the alkylation reaction. This excess of the aromatic hydrocarbon is maintained to reduce the production of polyalkylated benzene and to reduce the amount of olefin polymerization which occurs in the reaction zone. This preference also holds true for the first alkylation stage of the subject process, and the mole ratio of benzene or other feed aromatic hydrocarbon to the feed monoolefin at the point of initial olefin-acid contact should therefore be maintained above 1:1. Preferably this ratio is above 5:1 but below 12:1, with commercial operating ratios varying from about 3:1 to about 8:1. Although it is an object of the subject process to produce dialkylated aromatic hydrocarbons, it is preferred that these substantial benzene to olefin ratios be maintained in the first alkylation stage of the subject process. This is basically to minimize the amount of the olefinic hydrocarbon which is consumed in the production of byproducts such as dimers and trimers. In the second alkylation stage, and any subsequent alkylation stages, it is preferred that the ratio of total alkylaromatic to acyclic olefinic hydrocarbon is maintained above 1:1. This high ratio is desired to minimize the formation of polymer-type by-products and to thereby increase the selectivity of the process to the production of dialkylated aromatic hydrocarbons. However, it is specifically preferred that the mole ratio of the total of the aromatic hydrocarbons to the total acyclic olefinic feed hydrocarbon is maintained below 2.5:1 and that the mole ratio of unalkylated feed aromatic hydrocarbon to monoalkylated aromatic hydrocarbon is less than about 1:1. More preferably, this last ratio is below 0.75:1.

The aromatic hydrocarbon which is alkylated in the subject process is preferably benzene, but may be a higher molecular weight aromatic hydrocarbon. The feed aromatic hydrocarbon may therefore be toluene, a xylene, ethylbenzene, naphthalene, or a mixture of aromatic hydrocarbons such as a mixture of benzene and toluene. The feed olefinic hydrocarbon may be one or more acyclic monoolefin having from about 6 to about 22 carbon atoms per molecule. The preferred olefinic hydrocarbons are normal monoolefins having from 8 to about 15 carbon atoms per molecule. When these olefinic hydrocarbons are produced in a dehydrogenation process which is integrated with the alkylation process, it is a common practice to have the unseparated paraffin/olefin mixture produced as the stripped effluent stream of the dehydrogenation process pass directly into the alkylation zone as the olefin feed stream. This is basically because of the high cost of separating olefins and paraffins with the same carbon number. The feed olefin stream charged to the alkylation zone of the subject process may therefore contain from about 30 to about 70 mole percent paraffins having the same number of carbon atoms per molecule as the olefinic hydrocarbons. These relatively nonreactive paraffins pass through the alkylation zone and are separated from the alkylate by fractionation. The paraffins may then be recycled to the dehydrogenation zone.

The catalyst employed in the subject process is preferably substantially anhydrous liquid phase hydrogen fluoride. This HF catalyst preferably contains less than 5 weight percent water. The HF utilized in both the first alkylation stage and the second alkylation stage should contain at least 85 wt. % HF. The HF utilized in the first alkylation stage is preferably between about 85 to 95 wt. % HF and will typically be around 90 wt. % HF. The acid used in the second alkylation stage preferably contains more than 90 wt. % HF and is typically from about 93 to 97 wt. % HF. The higher purity of the acid utilized in the second alkylation stage is achieved through the passage of "regenerated" HF into the second alkylation stage from an HF regeneration zone. This HF regenerator is described below and basically effects the removal of high boiling compounds sometimes referred to as acid-soluble oil from the HF. The regenerated HF may be passed directly into the reaction zone of the second alkylation stage or may be utilized to contact the effluent of the reaction zone of the second alkylation stage. This contacting, which may be performed in a countercurrent manner, is normally beneficial in the production of detergents because it will effect a defluorination of the alkylate product and the extraction of naphthalene and anthracene. Although in a limited embodiment of the subject process high boiling hydrocarbons recovered from the used HF are admixed into the alkylate product, this contacting with an enriched HF stream would still be preferred for use in the subject process to effect a defluorination of the hydrocarbon discharged from the second alkylation stage.

Chemical reactions which involve olefinic hydrocarbons and which are catalyzed by HF usually proceed at a very fast rate. To reduce the amount of olefin polymerization and to promote the production of a monoalkylated aromatic product, the reactants are normally subjected to vigorous mixing and agitation at the point of initial contact of the olefinic hydrocarbons and the liquid phase HF. The desired result is a uniform dispersion and intimate contacting of the hydrocarbon and HF phases and the avoidance of localized high temperatures or localized high concentrations of either the olefinic hydrocarbon or the HF. The initial contacting of the reactants and the catalyst has been done in a number of different ways. For instance, the olefinic hydrocarbons have been sprayed into a mixture of HF and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The effluent streams leaving the reaction zone of the alkylation stages will typically be an intimate admixture of liquid phase hydrocarbons and liquid phase HF. They may be in the form of a true emulsion. A considerable residence time is normally required to separate these two liquid phases, and the effluent streams are therefore passed into settling zones.

The two settling zones will normally be maintained at a temperature which is set by the entering HF-hydrocarbon mixtures withdrawn from the respective upstream zones. They will therefore be at substantially the same temperature as the immediately upstream reaction zone. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 30 seconds but less than 30 minutes.

Those skilled in the alkylation art are familiar with the regeneration of the HF acid-catalysts. Information about the apparatus and conditions utilized for this operation is contained in the previously cited patents and also in U.S. Pat. Nos. 3,721,720 and 3,975,164. The regeneration operation is normally accomplished by stripping the acid under conditions sufficient to decompose alkylfluorides and to produce an overhead vapor stream containing HF and the stripping media. Benzene available within the process is a suitable stripping media. Heretofore, the overhead vapor stream of the column used to regenerate the HF was passed into a condenser. The resultant condensate was then allowed to separate into an acid phase and a benzene phase containing dissolved HF. The acid phase was withdrawn as the regenerated HF stream used in the contacting zone.

The subject process may accordingly be characterized as a process for the production of alkylated hydrocarbons which comprises the steps of passing a first feed stream which comprises a $C_6$-plus normal paraffinic hydrocarbon and a hereinafter characterized first recycle stream into a catalytic dehydrogenation zone and thereby producing a dehydrogenation zone effluent stream which comprises a mixture of the $C_6$-plus normal paraffinic hydrocarbon and a corresponding normal olefinic hydrocarbon; passing a first portion of the dehydrogenation zone effluent stream and a second feed stream which comprises an aromatic hydrocarbon into the first alkylation stage of a multi-stage alkylation zone maintained at alkylation-promoting conditions and thereby producing a first alkylation stage effluent stream which comprises the feed aromatic hydrocarbon, the normal paraffinic hydrocarbon and a monoalkylated aromatic hydrocarbon; passing the first alkylation stage effluent stream, a hereinafter characterized second recycle stream, and a second portion of the dehydrogenation zone effluent stream into the second alkylation stage of the alkylation zone maintained at alkylation-promoting conditions and thereby effecting the production of a second alkylation stage effluent stream which comprises the feed aromatic hydrocarbon, the normal paraffinic hydrocarbon, a monoalkylated aromatic hydrocarbon and a dialkylated aromatic hydrocarbon; fractionating the second alkylation stage effluent stream in a fractionation zone and thereby producing a first process stream which is rich in the monoalkylated and dialkylated aromatic hydrocarbons, a second process stream which is rich in the feed aromatic hydrocarbon and a third process stream which is rich in the normal paraffinic hydrocarbon; passing at least a portion of said third process stream into the dehydrogenation zone as the previously referred to first recycle stream; passing at least a portion of said second process stream into the alkylation zone; and withdrawing a first portion of said first process stream from the process as a product stream comprising a mixture of mono- and dialkylated aromatic hydrocarbons, and passing a second portion of the first process stream into the second alkylation stage of the alkylation zone as the previously referred to second recycle stream.

The hydrocarbon phase withdrawn from the settler of the terminal alkylation stage is the net effluent stream of the alkylation zone. This effluent stream is preferably passed into a fractionation zone which is designed and operated to concentrate entering mono- and dialkylated aromatic hydrocarbons into a first process stream and to produce at least one primary recycle stream. The necessary or primary recycle stream comprises a mixture of the mono- and dialkylated aromatic hydrocarbons and is preferably formed by dividing the first process stream into two portions, one of which becomes the recycle stream and the other becoming the product stream of the fractionation zone. The primary recycle stream could however be withdrawn directly off a fractionation column if so desired. In addition to the product stream and primary recycle stream, the fractionation zone will preferably also produce a second process stream which is rich in the feed aromatic hydrocarbon. This process stream is recirculated to the initial alkylation stage. The olefinic hydrocarbon feed stream will typically contain paraffins of the same number of carbon atoms of the feed olefin. These paraffins are the residual undehydrogenated feed to the dehydrogenation zone. It is less expensive to use this mixture as the feed olefin stream than to separate the olefinic and paraffinic hydrocarbons. As a result, unless a feed olefin stream having a very high purity is available, the unseparated dehydrogenation zone effluent stream is used as the olefinic feed stream. These paraffinic hydrocarbons are separated from the product hydrocarbons and the feed aromatic hydrocarbons in the fractionation zone to produce a paraffin-rich stream. In the preferred mode of operation, in which the alkylation zone is integrated with a paraffin dehydrogenation zone, this paraffin stream is passed into the dehydrogenation zone as an additional recycle stream. As used herein, any reference to a stream as being rich in a particular chemical compound or class of compounds, such as paraffins, is intended to indicate that the stream contains over 50 mole percent of the specified chemical compound or class of compounds.

The fractionation zone preferably comprises two reboiled fractionation columns as shown in the drawing. More than two columns could be employed if desired. These two columns are preferably operated in a similar manner to the first two fractionation columns employed in previously cited U.S. Pat. No. 3,950,448. The effluent stream of the alkylation zone is therefore preferably passed into a first column referred to as a benzene column or stripping column. The net overhead of this column is rich in the residual feed aromatic hydrocarbon and is referred to herein as the second process stream. The net bottoms stream of the first column therefore comprises a mixture of mono- and dialkylated hydrocarbons and the paraffinic hydrocarbons. This stream is then passed into a second column referred to as the paraffin column. This column produces a net overhead stream which is rich in the paraffinic hydrocarbons. The remainder of the material entering the paraffin column is concentrated into a net bottoms stream. A first portion of this bottoms stream is removed as the alkylate product for passage into storage or subsequent processing steps. This product should contain at least 25 mole percent dialkylated aromatics and preferably contains from about 35 to about 85 mole percent dialkylated aromatic hydrocarbons. The remainder of this product stream will be mainly the monoalkylated aromatic hydrocarbon but will also contain some reaction by-products produced by the dimerization or trimerization of the feed olefinic hydrocarbon.

In the subject process, a mixture of mono- and dialkylated aromatics is withdrawn from the fractionation zone and passed into the second alkylation stage. This mixture is referred to herein as the second recycle stream when referring to embodiments which also recycle paraffinic hydrocarbons to a dehydrogenation zone. This stream is preferably formed by dividing the net bottoms stream into two portions, one of which is recycled and the other being withdrawn as product. Those skilled in the art will recognize that this recycle stream could be formed in other ways. For instance, as previously specified, it could be withdrawn from the paraffin column as a sidecut stream. The product stream will then be the entire net bottoms of the paraffin column.

This primary recycle stream is necessary to achieve the desired production of dialkylated aromatics. Merely increasing the amount of olefinic hydrocarbons present in the alkylation reactors, as by reducing the total aromatics to olefin mole ratio, has been found to result in an undesirable large increase in the rate of olefin oligomerization. For this reason, monoalkylated aromatic hydrocarbons are recycled to increase the ratio of monoalkylated hydrocarbons to feed olefinic hydrocarbons. As the dialkylated aromatics are not adversely affected by passage through an alkylation reaction, it is not necessary to separate the dialkylated aromatics from the monoalkylated aromatics before the monoalkylated aromatics are recycled to the alkylation reaction zone. The amount of recycling required to meet the previously set out ratio of aromatic hydrocarbons to olefinic hydrocarbons may vary depending on such factors as feed stream composition, conversion rates and selectivities, etc. The rate of recycling may also be varied to influence the ratio of mono- to dialkylates in the final product stream. That is, the recycle rate of monoalkylated aromatics may be increased to increase the conversion of monoalkylated aromatics to dialkylated aromatics. To achieve the desired product mixture, at least 25 mole percent of the monoalkylated aromatic hydrocarbons which enter the fractionation zone as a part of the alkylation zone effluent stream are recycled to the alkylation zone. More preferably at least 35 mole percent of the monoalkylated aromatics are recycled.

The recycled monoalkylated aromatics are preferably not charged into the first alkylation stage. Rather, the first alkylation stage is operated to produce only the monoalkylated aromatic hydrocarbon and is therefore operated at a relatively high ratio of the feed aromatic hydrocarbon to the feed olefin.

The product stream of the subject process is preferably passed through a sulfonation zone wherein at least a majority of the mono- and dialkylated aromatics are converted to a corresponding sulfonate. These sulfonates may be sodium, lithium, potassium, or ammonium salts. However, if so desired, the product stream produced in the fractionation zone may be discharged from the process without any further chemical reaction. Other alternatives are the conversion of the mono- and dialkylaromatics into alcohols, ethoxylated alcohols including polyethoxylated alkylphenols, alkylpolyalkoxyalkylene sulfonates or alkylarylpolyalkoxyalkylene sulfonates. It would be quite expensive to separate the various components of the fractionation zone effluent product stream and the subsequent chemical conversion of this mixture to produce any of these just mentioned types of chemical compounds will produce a variety of compounds. This is especially true because the product stream will normally contain a mixture of acyclic compounds produced by olefin oligomerization in addition to the desired alkylaromatics.

In the sulfonation zone, the product stream from the fractionation zone is contacted with a sulfonating agent such as sulfur trioxide, sulfuric acid, alkali disulfides and mixtures of sulfur dioxide and sulfur trioxide at sulfonation-promoting conditions. Anhydrous sulfur trioxide is the preferred sulfonation agent, with the sulfur trioxide preferably being passed into a reactor in admixture with air at mild conditions which tend to result in the production of monosulfonates rather than disulfonates. A relatively low temperature and sulfur trioxide concentration are therefore preferred. The preferred conditions include a superatmospheric pressure sufficient to ensure the hydrocarbons are in the liquid phase but generally less than about 10 atmospheres absolute and a temperature between about 15° and 150° C. From about 5 to about 30 kg of sulfur trioxide may be passed through the reaction zone for every 100 kg of aromatic hydrocarbons.

The intended products of the sulfonation reaction are sulfonic acids. These acids and the other normally liquid compounds present in the effluent of the sulfonation zone may be processed at this point to separate oil-soluble sulfonic acids from water-soluble sulfonic acids. Preferably, at least a portion of the effluent of the sulfonation reactor is neutralized as by the passage of this material into a saponification zone. This typically comprises the admixture of the sulfonation reactor effluent material with an aqueous stream containing ammonia, sodium hydroxide or potassium hydroxide. The alkaline compound neutralizes the sulfonic acid to produce sulfonates such as sodium alkylaromatic monosulfonate salts. Again the effluent of this neutralization step can be used directly, as for an enhanced oil recovery surfactant, or the effluent can be subjected to separation steps to obtain a higher purity of a desired product. For instance, it is common practice to pass the effluent of a saponification zone into an extraction zone wherein the sulfonates are extracted from unreacted hydrocarbonaceous compounds with an aqueous mixture of an alkylalcohol, with 25 to 60 wt. % isopropanol being preferred as the solvent. The isopropanol solution can then be easily stripped from the extract stream to yield the sulfonates. Further information on sulfonation and saponification can be obtained from standard references, the previously cited patents and U.S. Pat. Nos. 4,036,875 and 4,240,978.

The normal paraffin stream which is preferably, but not necessarily, produced in the fractionation zone is preferably recycled to a catalytic paraffin dehydrogenation zone. In this zone, the paraffins in admixture with hydrogen are contacted with a catalyst at an elevated temperature to produce additional feed olefinic hydrocarbons. A preferred set of dehydrogenation conditions includes a temperature of about 420° to about 545° C., a pressure from about 0.7 to about 13 atmospheres absolute (preferably about 2.0) and a liquid hourly space velocity in the range of about 10 to 36. A catalyst comprising platinum, tin and chlorine supported on alumina spheres is preferred although other catalysts can be substituted. The recycled paraffins together with any feed paraffins charged to the overall process are heated to reaction conditions and preferably passed through a single catalyst bed. The effluent of the catalyst bed is partially condensed to allow a simple separation of a hydrogen-rich gas, a portion of which is withdrawn with the remainder being recycled to the reactor. The net condensate is passed into a stripping column wherein all hydrocarbons having fewer carbon atoms per molecule than the desired feed normal olefin(s) are removed overhead as a light ends stream. Further details on suitable dehydrogenation methods may be obtained by reference to U.S. Pat. Nos. 3,391,218; 3,448,165; 3,745,112; and 3,907,921. The catalyst and the configuration of the dehydrogenation reaction zone may be chosen as desired from any commercially feasible type of catalyst and reactor.

We claim as our invention:

1. A process for the production of dialkylated aromatic hydrocarbons which comprises the steps of:
   (a) alkylating a feed aromatic hydrocarbon with a first portion of a feed acyclic olefinic hydrocarbon in a first alkylation stage of a multi-stage alkylation zone maintained at alkylation-promoting conditions to produce a first alkylation stage effluent stream which comprises the feed aromatic hydrocarbon and a monoalkylated aromatic hydrocarbon;
   (b) admixing the first alkylation stage effluent stream, a hereinafter characterized recycle stream and a second portion of the feed acyclic olefinic hydrocarbon to form a composite stream, said composite stream having a mole ratio of unalkylated aromatic hydrocarbon to monoalkylated aromatic hydrocarbon of less than about 1:1, and passing said composite stream into a subsequent second alkylation stage of the alkylation zone maintained at alkylation-promoting conditions to further alkylate said monoalkylated aromatic hydrocarbons and to produce a second alkylation stage effluent stream which comprises the feed aromatic hydrocarbon, the monoalkylated hydrocarbon, and a dialkylated hydrocarbon;
   (c) fractionating said alkylation zone effluent stream which comprises the feed aromatic hydrocarbon, the monoalkylated hydrocarbon, and the dialkylated hydrocarbon in a fractionation zone, to produce a first process stream which comprises the monoalkylated aromatic hydrocarbon and the aromatic dialkylated hydrocarbon; and,
   (d) withdrawing a first portion of the first process stream as a product stream containing said dialkylated aromatic hydrocarbon and passing a second portion of the first process stream into the second alkylation stage of said alkylation zone as the previously referred to recycle stream to form said composite stream having a mole ratio of unalkylated feed aromatic hydrocarbon to monoalkylated aromatic hydrocarbon of less than about 1:1 to increase the production of dialkylated aromatic hydrocarbons.

2. The process of claim 1 further characterized in that a second process stream, which is rich in the feed aromatic hydrocarbon, is produced in said fractionation zone and is passed, at least in part, into said first alkylation stage of said alkylation zone.

3. The process of claim 2 further characterized in that a third process stream, which is rich in a normal paraffinic hydrocarbon, is produced in said fractionation zone, and at least a portion of the third process stream is passed into a dehydrogenation zone, wherein a portion of the normal paraffinic hydrocarbons are dehydrogenated to produce said acyclic olefinic hydrocarbons consumed in the alkylation zone.

4. The process of claim 3 further characterized in that the feed aromatic hydrocarbon is selected from the group consisting of benzene and toluene.

5. The process of claim 4 further characterized in that the feed acyclic olefinic hydrocarbon comprises a $C_6$ to $C_{22}$ normal monoolefinic hydrocarbon.

6. The process of claim 5 further characterized in that the product stream comprises between 35 and 85 mole percent dialkylated aromatic hydrocarbons.

7. The process of claim 2 further characterized in that the feed acyclic olefinic hydrocarbon is a branched chain acyclic olefin.

8. The process of claim 1 further characterized in that the alkylation reaction is promoted by a catalyst which comprises liquid phase HF.

9. The process of claim 8 further characterized in that the alkylation zone contains only two alkylation stages.

10. A process for the production of dialkylated aromatic hydrocarbons which comprises the steps of:
   (a) passing a first feed stream which comprises a $C_6$-plus normal paraffinic hydrocarbon and a hereinafter characterized first recycle stream into a catalytic dehydrogenation zone to produce a dehydrogenation zone effluent stream which comprises a mixture of the $C_6$-plus normal paraffinic hydrocarbon and a corresponding normal olefinic hydrocarbon;
   (b) passing a first portion of the dehydrogenation zone effluent stream and a second feed stream which comprises an aromatic hydrocarbon into a first alkylation stage of a multi-stage alkylation zone maintained at alkylation-promoting conditions to produce a first alkylation stage effluent stream which comprises the feed aromatic hydrocarbon, the normal paraffinic hydrocarbon and a monoalkylated aromatic hydrocarbon;
   (c) admixing the first alkylation stage effluent stream, a hereinafter characterized second recycle stream, and a second portion of the dehydrogenation zone effluent stream to form a composite stream, said composite stream having a mole ratio of unalkylated aromatic hydrocarbon to monoalkylated aromatic hydrocarbon of less than about 1:1, and passing said composite stream into a second alkylation stage of the alkylation zone maintained at alkylation-promoting conditions to further alkylate said monoalkylated aromatic hydrocarbon and to produce a second alkylation stage effluent stream which comprises the feed aromatic hydrocarbon, the normal paraffinic hydrocarbon, a monoalkylated aromatic hydrocarbon and a dialkylated aromatic hydrocarbon;

(d) fractionating the second alkylation stage effluent stream in a fractionation zone to produce a first process stream which is rich in the monoalkylated and dialkylated aromatic hydrocarbons, a second process stream which is rich in the feed aromatic hydrocarbon and a third process stream which is rich in the normal paraffinic hydrocarbon;

(e) passing at least a portion of said third process stream into the dehydrogenation zone as the previously referred to first recycle stream of step (a);

(f) passing at least a portion of said second process stream into the first alkylation stage of said alkylation zone; and (g) withdrawing a first portion of said first process stream from the process as a product stream containing said dialkylated aromatic hydrocarbons, and passing a second portion of the first process stream into the second alkylation stage of the alkylation zone as the previously referred to second recycle stream to form said composite stream having a mole ratio of unalkylated feed aromatic hydrocarbon to monoalkylated aromatic hydrocarbon of less than about 1:1 to increase the production of said dialkylated aromatic hydrocarbons.

11. The process of claim 10 further characterized in that the alkylation reaction is promoted by a catalyst which comprises liquid phase HF.

12. The process of claim 10 further characterized in that the product stream comprises over 25 mole percent dialkylated aromatic hydrocarbons.

13. The process of claim 12 further characterized in that the feed aromatic hydrocarbon is selected from the group consisting of benzene and toluene.

14. The process of claim 13 further characterized in that the normal paraffinic hydrocarbon and the normal olefinic hydrocarbon have between 8 and 20 carbon atoms per molecule.

15. The process of claim 14 further characterized in that the product stream contains from about 35 to about 85 mole percent dialkylated aromatic hydrocarbons.

16. The process of claim 14 further characterized in that a portion of a stream of liquid phase HF withdrawn from the second alkylation stage of the alkylation stage is passed into a fractionation column operated at regeneration conditions and at least a portion of the net bottoms stream of the fractionation column is admixed into the product stream.

* * * * *